United States Patent
Chu

(10) Patent No.: US 11,241,268 B2
(45) Date of Patent: Feb. 8, 2022

(54) ELECTROSURGERY DEVICES AND METHODS FOR PROVIDING ELECTRIC ENERGY TREATMENT

(71) Applicant: Boston Scientific Scimed, Inc., Maple Grove, MN (US)

(72) Inventor: Michael S. H. Chu, Brookline, MA (US)

(73) Assignee: Boston Scientific Scimed. Inc., Maple Grove, MN (US)

( * ) Notice: Subject to any disclaimer, the term of this patent is extended or adjusted under 35 U.S.C. 154(b) by 712 days.

(21) Appl. No.: 15/956,597

(22) Filed: Apr. 18, 2018

(65) Prior Publication Data

US 2018/0317996 A1 Nov. 8, 2018

Related U.S. Application Data

(63) Continuation of application No. 14/565,667, filed on Dec. 10, 2014, now Pat. No. 9,974,553.

(60) Provisional application No. 61/923,475, filed on Jan. 3, 2014.

(51) Int. Cl.
*A61B 18/12* (2006.01)
*A61B 18/14* (2006.01)
*A61B 17/221* (2006.01)
*A61B 18/00* (2006.01)

(52) U.S. Cl.
CPC .......... *A61B 18/1206* (2013.01); *A61B 18/14* (2013.01); *A61B 18/1492* (2013.01); *A61B 2017/2215* (2013.01); *A61B 2018/0016* (2013.01); *A61B 2018/00214* (2013.01); *A61B 2018/00589* (2013.01); *A61B 2018/00595* (2013.01); *A61B 2018/00601* (2013.01); *A61B 2018/141* (2013.01)

(58) Field of Classification Search
CPC . A61B 18/1206; A61B 18/14; A61B 18/1492; A61B 2018/00589; A61B 2018/00595; A61B 2018/00601; A61B 2018/0016; A61B 2018/00214; A61B 2018/141; A61B 2017/2215
USPC ........................................................ 606/41
See application file for complete search history.

(56) References Cited

U.S. PATENT DOCUMENTS

| | | | |
|---|---|---|---|
| 3,955,578 A | | 5/1976 | Chamness et al. |
| 3,984,790 A | * | 10/1976 | Tanaka ..................... H03H 9/09 333/200 |
| 4,493,320 A | | 1/1985 | Treat |
| 5,078,716 A | | 1/1992 | Doll |
| 5,437,665 A | * | 8/1995 | Munro ................... A61B 18/14 606/41 |

(Continued)

*Primary Examiner* — Linda C Dvorak
*Assistant Examiner* — Nils A Potter
(74) *Attorney, Agent, or Firm* — Bookoff McAndrews, PLLC

(57) ABSTRACT

A medical device including an energy generator, a proximal end, and a distal end. The proximal end may include a handle and one or more connectors coupled to the energy generator. The distal end may include a number of movable branch members connected to one or more movable filaments at the distal end to form at least one expandable snare. At least one of the one or more movable filaments may be coupled to the one or more connectors to transfer energy to the at least one of the one or more movable filaments. A portion of the at least one of the one or more movable filaments forming the at least one expandable snare may be insulated.

14 Claims, 5 Drawing Sheets

(56) References Cited

U.S. PATENT DOCUMENTS

| | | | |
|---|---|---|---|
| 5,702,438 A | 12/1997 | Avitall | |
| 5,906,622 A | 5/1999 | Lippitt et al. | |
| 5,924,175 A | 7/1999 | Lippitt et al. | |
| 6,152,936 A | 11/2000 | Christy et al. | |
| 6,517,539 B1 | 2/2003 | Smith et al. | |
| 6,527,769 B2 | 3/2003 | Langberg et al. | |
| 6,537,273 B1 * | 3/2003 | Sosiak | A61B 18/14 606/170 |
| 6,743,228 B2 * | 6/2004 | Lee | A61B 8/0825 606/113 |
| 6,986,767 B2 | 1/2006 | Durgin et al. | |
| 7,041,108 B2 * | 5/2006 | Lippitt | A61B 17/221 604/264 |
| 7,101,378 B2 * | 9/2006 | Salameh | A61B 17/32056 600/564 |
| 7,210,210 B2 | 5/2007 | Lippitt et al. | |
| 7,611,510 B2 * | 11/2009 | Canady | A61B 18/042 606/45 |
| 7,819,872 B2 * | 10/2010 | Johnson | A61B 17/320016 606/51 |
| 8,328,803 B2 | 12/2012 | Regadas | |
| 9,724,113 B2 | 8/2017 | Chu | |
| 2002/0068944 A1 | 6/2002 | White et al. | |
| 2004/0215212 A1 | 10/2004 | Teague et al. | |
| 2007/0060920 A1 * | 3/2007 | Weitzner | A61B 18/16 606/39 |
| 2009/0182324 A1 | 7/2009 | Kurtulus | |
| 2009/0248008 A1 | 10/2009 | Kerr | |
| 2011/0087222 A1 | 4/2011 | Miller et al. | |
| 2011/0112548 A1 * | 5/2011 | Fifer | A61B 17/320016 606/129 |
| 2012/0172864 A1 | 7/2012 | Farin et al. | |
| 2012/0330295 A1 | 12/2012 | Manwaring | |
| 2014/0276908 A1 * | 9/2014 | Raybin | A61B 17/32056 606/113 |
| 2015/0066047 A1 | 3/2015 | Chu | |
| 2015/0148814 A1 | 5/2015 | Chu | |
| 2015/0164522 A1 | 6/2015 | Budiman et al. | |
| 2016/0022291 A1 * | 1/2016 | Johnson | A61B 8/12 606/113 |

\* cited by examiner

ELECTROSURGERY DEVICES AND METHODS FOR PROVIDING ELECTRIC ENERGY TREATMENT

CROSS-REFERENCE TO RELATED APPLICATIONS

This application is a Continuation of U.S. patent application Ser. No. 14/565,667, filed Dec. 10, 2014, which claims the benefit from U.S. Provisional Application No. 61/923,475, filed on Jan. 3, 2014, each of which being incorporated by reference herein in their entireties.

TECHNICAL FIELD

The present disclosure relates generally to surgical instruments and related systems and methods. More particularly, the present disclosure relates to adjustable electrosurgery devices, systems, and methods for providing treatment of human tissue.

BACKGROUND

Medical devices are often used to extract undesired and/or foreign material from the body. These medical devices use various extraction methods, such as dissection, coagulation fulguration, ablation, etc., of undesired body matter. An example of a type of procedure that uses such methods is electrosurgery. Electrosurgery involves the application of energy to biological tissue to cut, coagulate, desiccate, or fulgurate tissue. Electrosurgery uses various types of high-frequency electrical energy to directly heat the tissue.

Conventional electrosurgical devices often require many small and complex components. Assembly of these small and complex components may require significant effort and labor, which may increase manufacturing time and costs. Further, due to the presence of many components, these conventional devices may have many weak points at which the device may be prone to breakage. Another problem with many conventional electrosurgical devices is that they have large profiles and are not configured to capture and extract smaller objects in difficult to reach areas of the body. In addition, conventional electrosurgical devices may be prone to short circuit. Therefore, a need exists for a medical device with fewer parts that is configured to safely perform electrosurgical procedures.

SUMMARY

The disclosed embodiments relate to surgical devices and methods of using and manufacturing the same for providing electric energy treatment of human tissue through a working channel of scope, a natural orifice, or by incision.

One exemplary embodiment may include a surgical device having an energy generator, a proximal end, and a distal end. The proximal end may include a handle and one or more connectors coupled to the energy generator. The distal end may include a number of movable branch members connected to one or more movable filaments at the distal end to form at least one expandable snare. Further, at least one of the one or more movable filaments may be coupled to the one or more connectors to transfer energy to the at least one of the one or more movable filaments. Furthermore, a portion of the at least one of the one or more movable filaments forming the at least one expandable snare is insulated.

This exemplary device may further include one or more of the following features: a portion of the one or more movable filaments is secured to a distal end of one of the plurality of movable branch members; the insulated portion of the one or more movable filaments is located where the filament is secured to the distal end of the one of the plurality of movable branch members is insulated; one half of the at least one expandable snare is insulated; portions of the one or more movable filaments proximal of the at least one expandable snare are insulated; the one or more movable filaments comprise a plurality of movable filaments having portions forming a plurality of expandable snares; portions of the plurality of movable filaments proximal of the plurality of expandable snares are insulated; portions of the plurality of expandable snares vertically aligned with each other are insulated; each of the plurality of expandable snares are connected to a different connector of one of the one or more connectors a distal one of the plurality of snares is configured to transfer energy, and a proximal one of the plurality of snares does not transfer energy and is configured to capture matter; portions of the one or more movable filaments are disposed in a lumen of at least one of the plurality of movable branch members and are insulated; the one or more connectors comprises one electrical connector configured to provide electrical energy to the at least one expandable snare and the medical device further comprises a return electrode configured to connect to an external surface of a patient; at least one of the plurality of branch members has a distal end proximal to the distal end of the other plurality of branch members; the energy generator is electrical voltage; distal portions of the plurality of branch members have a preset shape to an expanded configuration spaced away from a central longitudinal axis of the device; the handle further comprises an actuator operatively coupled to the plurality of movable filaments and configured to provide a tensioning force on the proximal ends of the plurality of movable filaments to collapse the expandable snare and move the plurality of movable branch members toward the central longitudinal axis; distal portions of the plurality of branch members have a natural linear shape; the handle further comprises an actuator operatively coupled to the plurality of movable filaments and configured to provide a pushing force on the proximal ends of the plurality of movable filaments to expand the expandable snare from a collapsed configuration to a more expanded configuration.

An additional exemplary embodiment includes a surgical device that may include an energy generator 126, a proximal end, and a distal end. The proximal end may include a handle and one or more connectors coupled to the energy generator. The distal end may include a plurality of movable branch members connected to a plurality of movable filaments at a distal end to form a plurality of expandable snares. The plurality of movable filaments is coupled to the one or more connectors to transfer energy to the plurality of movable filaments and portions of the plurality of movable filaments forming the plurality of expandable snares are insulated.

Yet another exemplary embodiment is a medical device that may include an energy generator 126, a proximal end, and a distal end. The proximal end may include a handle and one or more connectors coupled to the energy generator. Further, the distal end may include a plurality of movable branch members connected to one or more movable filaments at a distal end to form an expandable snare, one of the plurality of branch members having a distal end proximal to a distal end of at least another one of the plurality of branch members.

The above summary of exemplary embodiments is not intended to describe each disclosed embodiment or every implementation of the present disclosure. The figures, and detailed description which follow, more particularly exemplify these exemplary embodiments.

BRIEF DESCRIPTION OF THE DRAWINGS

The drawings illustrate the design and utility of exemplary embodiments of the present disclosure, in which similar elements are referred to by common reference numerals. In order to better appreciate how the characteristics of the present disclosure can be obtained, a more detailed description of the present embodiments will be rendered by reference to the accompanying drawings. Understanding that these drawings depict only exemplary embodiments of the disclosure and are not therefore to be considered limiting in scope, the disclosure will be described and explained with additional specificity and detail through the use of the accompanying drawings in which.

DETAILED DESCRIPTION OF EXEMPLARY EMBODIMENTS

Reference will now be made in detail to exemplary embodiments of the present disclosure, examples of which are illustrated in the accompanying drawings. The term "distal" used herein refers to the direction that is away from the user and into the patient's body. By contrast, the term "proximal" refers to the direction that is closer to the user and away from the patient's body.

Exemplary embodiments of the present disclosure relate to systems, medical devices/surgical instruments, and methods for providing energy treatment to human tissue. The medical device may include at least one expandable snare and at least two movable branch members at a distal end of the device for contacting tissue within a human body. The expandable snare may be comprised of one or more movable filaments which may act as an electrode to deliver therapeutic energy to portions of the body, such as tissue. Portions of the movable filaments may be selectively insulated to prevent an electrical short circuit. In some embodiments some of the branch members may be shorter than other branch members to configure the expandable snare to have an angled shape when expanded.

The embodiments of the electrosurgical device may operate in two configurations, a monopolar configuration and a bipolar configuration, as described in detail with references to subsequent figures.

EXEMPLARY EMBODIMENTS

The following describes the interaction of the various components of the system 100 followed by a further description of each of the components.

Figure 1:
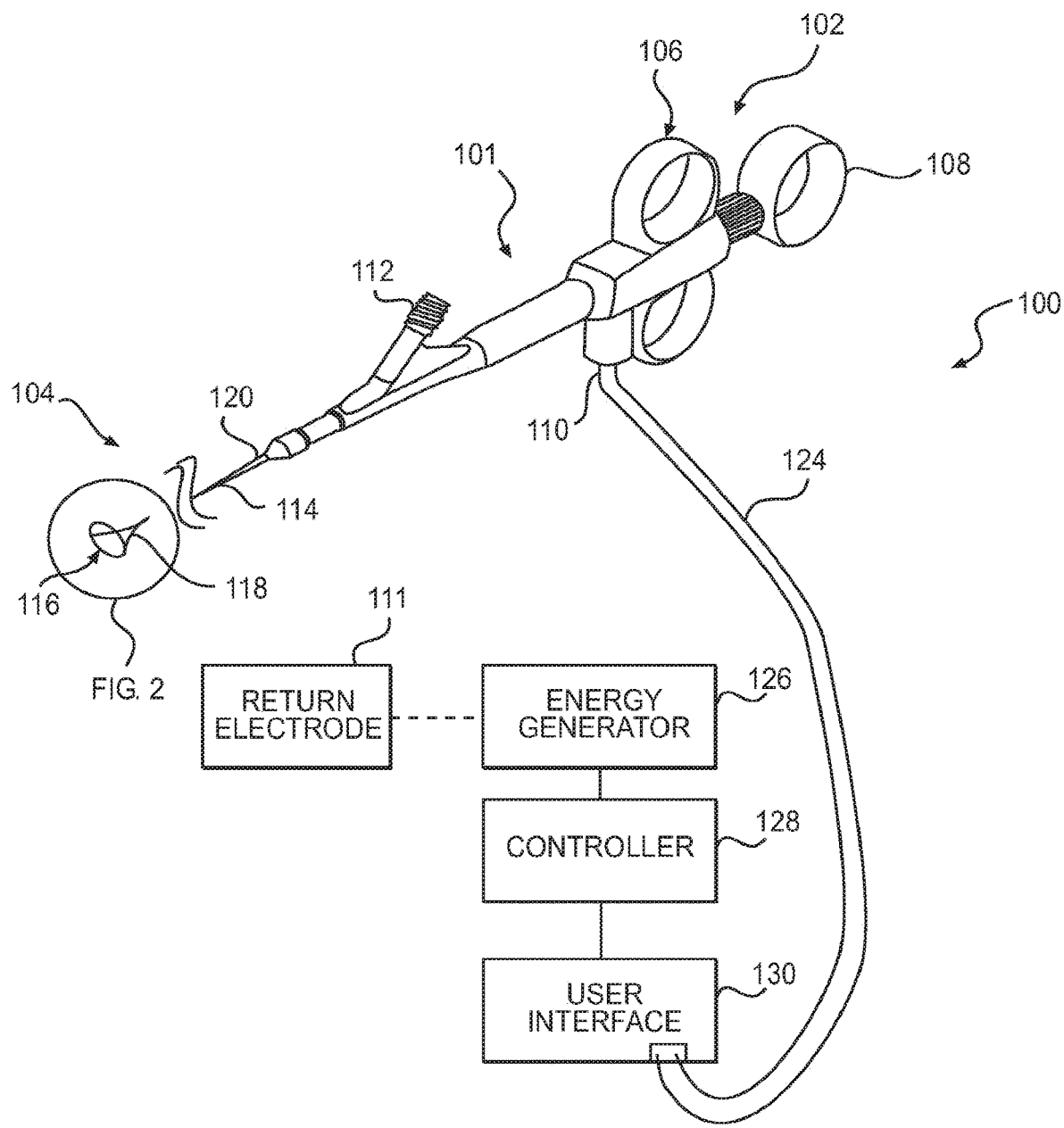
FIG. 1 illustrates an exemplary system including a medical device in accordance with various embodiments of the present disclosure.

FIG. 1 illustrates a schematic view of an exemplary system 100 including a medical device 101 for providing energy treatment of tissue, in accordance with various embodiments of the present disclosure. As shown, the medical device 101 may extend from a proximal end 102 towards a distal end 104. The proximal end 102 of the medical device 101 may include a handle 106 configured to be held by a user of the medical device 101. The handle 106 may include an actuator 108 configured to be manipulated by the user to actuate portions of the medical device 101. For example, to steer, expand, collapse, actuate, etc., one or more portions of the medical device 101. The medical device 101 may further include an injection port 112 for delivery of various suitable fluids. The injection port 112 on the handle 106 may be in fluid communication with a sheath 120 and an outlet port (not shown) near the distal end 104 of the medical device 101. The sheath 120 may be positioned between the proximal end 102 and distal end 104 of the medical device 100.

The proximal end 102 of the medical device 101 may also include a plug 110 for coupling to various components of the system 100. For example, the medical device 101 may be coupled via a plug 110 to an energy generator 126, a controller 128, and/or a user interface 130. The coupling of the plug 110 to the user interface 130, controller 128, and or the energy generator 126 may be via a lead 124.

The distal end 104 of the medical device 101 may be configured to transition from a collapsed configuration to an expanded configuration and vice versa, based on actuation of the actuator 108 on the handle 106. The actuator 108 may be coupled to a drive wire 114. A portion of the drive wire 114 may be housed in the sheath 120. A proximal portion of the drive wire 114 may be coupled to the actuator 108. The drive wire 114 also may be operatively coupled to the energy generator 126, for example electrically coupled via the plug 110 and the lead 124, and may be configured to transfer energy to components at the distal end 104 of the medical device 101.

A distal end of the drive wire 114 may be coupled to portions of an expandable snare 116 on the distal end 104 of the medical device 101. The expandable snare 116 may be configured to act as an electrode to transfer energy to portions of the patient's body (not shown).

In addition, the distal end 104 of the medical device 101 may include one or more branch members 118 coupled to the movable filament 122 forming the snare 116. The snare 116 is shown in FIG. 1 in an expanded configuration. The medical device 101 may be configured to operate in monopolar and/or bipolar mode. In the monopolar mode, portions of the expandable snare 116 may be connected to one terminal/connector of the energy generator 126 and another portion of the expandable snare 116 may be connected to a return electrode 111, such as a pad adjacent the patient.

Figure 2:
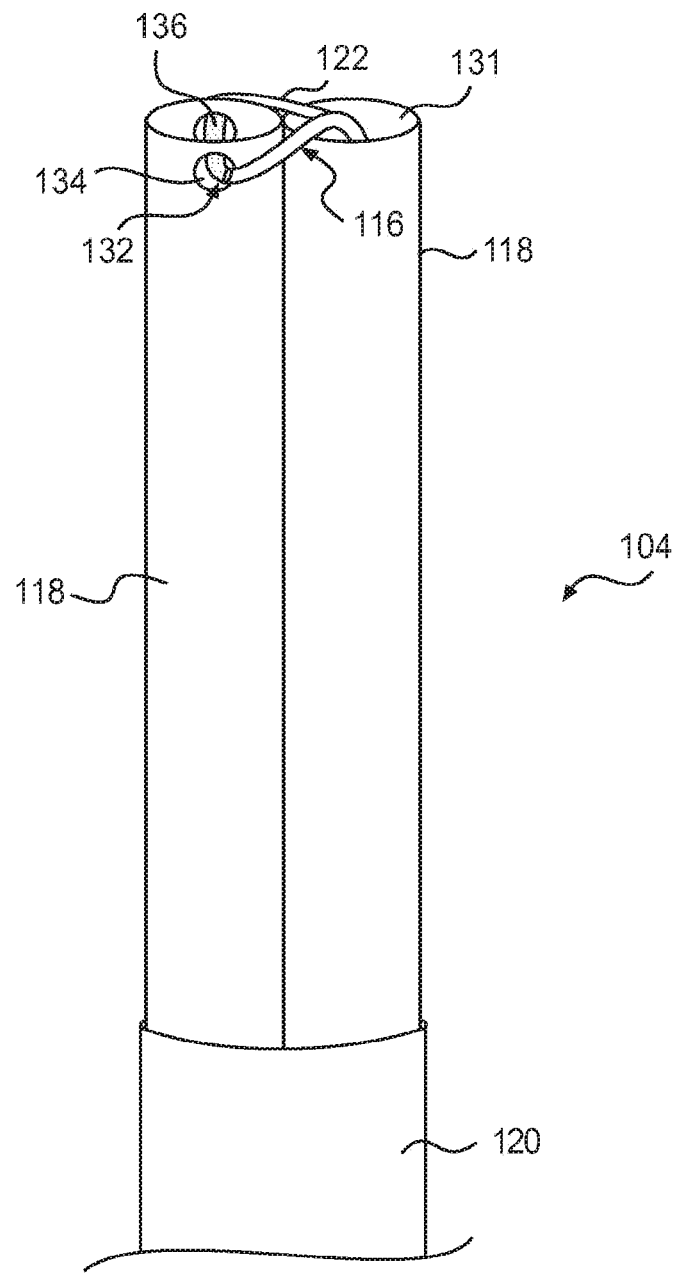
FIG. 2 illustrates a distal end of the exemplary medical device of FIG. 1 in a collapsed configuration.
Figure 3:
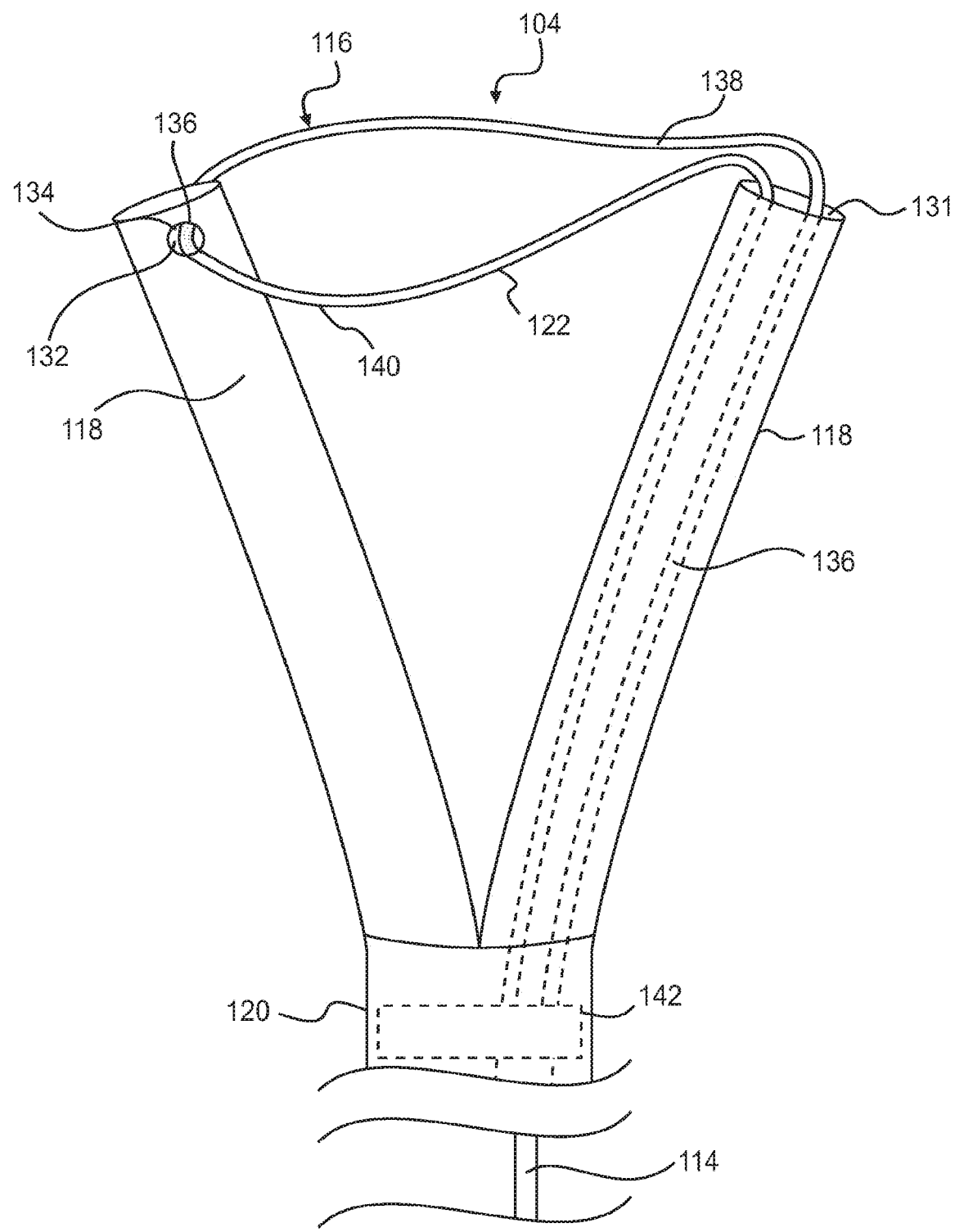
FIG. 3 a distal end of the exemplary medical device of FIG. 1 in an expanded configuration.

FIGS. 2 and 3 show the distal end 104 of the medical device 101 in further detail. FIG. 2 illustrates the distal end 104 of the medical device 101 in a collapsed configuration. In the collapsed configuration, the distal end 104 of the medical device 101 may be used as an electrode for use in delivery of therapeutic energy to tissue. As shown, in FIG. 2, a movable filament 122 forming the expandable snare 116, may be secured at a filament securing location 134 (e.g. a midpoint of the movable filament 122) in a distal aperture 132 of one of the branch members 118. The movable filament 122 may be secured to the branch member 118 at the filament securing location 134 by glue or by using any other suitable fixing arrangement. As shown in the FIG. 2, the fixing may be via the distal aperture 132 (e.g. hole, slot)

extending orthogonally through the branch member 118. The ends of the movable filament 122 may be inserted via distal opening 131 in another branch member 118.

Portions of the movable filament 122 may include an insulator 136. For example, the filament securing location 134 of the movable filament 122 may include the insulator 136. The insulating may be deposited or coated on the movable filament 122 in any suitable manner and have any suitable pattern. In some embodiments, the snare 116 may omit the insulator 136. FIGS. 1 and 2 illustrate the medical device 101 in monopolar mode, and illustrate a single snare 116 embodiment.

In an expanded configuration, as shown in FIG. 3, the movable branch members 118 connected to the filament 122 may form at least one expandable snare 116. In at least one embodiment, one half of the at least one expandable snare 116 may include insulator 136.

A first end 138 and a second end 140 of the movable filament 122 forming the snare 116 and extending within the lumen of one of the branch members 118 via the distal opening 131 may be coupled to one or more couplers 142 and connect to the drive wire 114. The couplers 142 may connect the two ends 138 and 140 of the movable filament 122 in any suitable manner, such as via a crimp, weld, knot, glue, etc. The one or more couplers 142 may include an electrical connector configured to provide electrical energy to the expandable snare 116, and the medical device 101.

The movable filament 122 may be coupled to the coupler 142 to transfer or supply energy to the movable filament 122. Some portions of the movable filament 122 forming the expandable snare 116 may be insulated using the electrical insulator 136 so that they are not short circuited when different portions of the snare 116 come in contact with each other.

The following is a further description of the components of the system 101.

The energy generator 126 may supply any suitable energy, such as electrical, laser, thermal, ultrasound, etc. The controller 128 and the user interface 130 may include various components, such as processors for processing instructions (e.g. program instructions), memory, and user input devices. The controller 128 and the user interface 130 may modulate the characteristics of the energy supplied to the medical device 101.

The lead 124 and plug 110 may have any suitable size shape and geometry and may be manufactured using any suitable materials proving insulation on the exterior of the lead 124 and the plug 110. The actuator may have any suitable form, such as finger rings, knobs, dials, levers, buttons, triggers, etc. The handle 106 may be manufactured using any suitable material(s), such as plastics and metals.

The injection port 112 may be configured to couple to a tube, syringe, or any other suitable fluid delivery device. A lumen formed in the medical device 101 may be used to inject various fluids, such as drugs or irrigation fluid to flush the lens of a scope. The sheath 120 may be manufactured using any suitable materials, such as polymers. The sheath may have any suitable properties, such as insulating properties.

The branch member 118 to which the movable filament 122 is secured, may be solid, and may have a smaller diameter than the other branch members 118. One or more ends, such as a first end 138 and a second end 140 (shown in FIG. 3), of the movable filament 122 may be disposed, and extend within a lumen formed in at least another movable branch member 118 via a distal opening 131 of that branch member 118.

In some embodiments, the branch members 118, may be substantially similar, and may be formed in a tubular shape, some, or all having a lumen. The branch members 118 may be formed of a polymer or a metal, such as PET, peek, polyimide, nitinol, stainless steel, or the like, and may include coating of electrically insulative material (or the insulator 136), such as, but not limited to, polytetrafluoroethylene, TEFLON, and the like.

The profile of the branch members 118 may be of any suitable shape, size, or geometry, such as round, square, rectangular, oval, or polygonal in cross sectional profile. In one embodiment, the one or more movable branch members 118 may have a very low profile when in a collapsed configuration. For example, each branch member 118 may have flat complimentary shaped surfaces, which may fit into each other when the branch members 118 are in the collapsed configuration. In another embodiment, (not shown), one or more of the branch members 118 may be shorter than other branch members 118, such that the distal end of one branch member may be proximal to the distal end of another branch member 118. In this configuration the expandable snare 116 may form an angle configuration and the medical device 101 may selectively access and treat body matter. The angle configuration also may allow the user to have directional control to direct the snare 116 towards side targets. For example, to position the snare 116 evenly or level with the foot of a polyp (to resect the entire polyp). In some embodiments, one or more of the branch members 18 may include a curve or be bent to have a similar directional control.

The proximal portions of the branch members 118 may be adjacent to one another and may be disposed within and extend from the sheath 120. The branch members 118 may be connected at the proximal portions of the sheath 120 using any suitable means or combination of means, such as heat shrinking, gluing, and heat bonding, or in any other preferred manner.

In some embodiments, the moveable filament 122 may include multiple movable filaments. In other embodiments, the movable filament 122 may be movably attached to each branch member 118 via an exterior surface feature of branch member 118. Examples of such exterior surface features may include grooves, hooks, protrusions, etc. to which the movable filament may couple to in any suitable manner e.g. adhesive, glue, knots, etc.

The movable filament 122 may be a single strand or filament wire, a monofilament or braided wire, a suture, rope, or the like. The movable filament 122 may be manufactured using any suitable material or combination of materials and may be flexible and have suitable properties to move the branch members 118 from a radially expanded position to a substantially linear position, either by transferring a tensioning force or a pushing force from the actuator 108, associated with the handle 106. The movable filament 122 may be a metal, a polymer, or a combination of materials such as a metal wire that is coated with a plastic (polymer) jacket, or for example, two metals co-drawn together. The movable filament 122 may have various properties including elasticity and flexibility, for reaching around various body matter and entrapping matter.

The movable filament 122 may be continuous from one end to the other end. In another example, the movable filament 122 may be manufactured by connecting multiple sections of same or different materials, profiles, properties, etc. The movable filament 122 may have a round, square, rectangular, oval, or polygonal in cross sectional profile. For example, the movable filament 122 may be a filament, a certain portion of which may be flattened, machined, removed, extruded, drawn, bent, notched, roughened, heat set, or etched to a different or preferred profile. In one example, the movable filament 122 may be a nitinol wire with an outside diameter of about 004".

The handle 106 may enable a user to control the movement of the filament 122 inwardly and outwardly through the movable branch members 118 to respectively expand and collapse the snare 116. The ends of the filament 122 may be connected directly to the handle 106 or by means of the drive wire 114 as shown. The sheath 120 attached to the branch members 118 at the distal end 104 may extend to connect to the handle 106 at the proximal end 102 of the medical device 101. The actuator 108 may be operatively coupled to the movable filament 122. In an embodiment, the branch members 118 may have a natural position in which the distal ends of the branch members 118 are substantially parallel to each other. In this embodiment, the actuator 108 may be configured to provide a pushing force on the drive wire 114 and the movable filaments 122. In response to this pushing force, the movable filament 122 may expand and the distal ends of the branch members 118 may radially move away from a longitudinal axis.

In another embodiment, the branch members 118 may have a natural position or preset shape in which the distal ends of the branch members 118 are radially spaced apart from the longitudinal axis and the snare 116 is in an expanded configuration. In this embodiment, the actuator 108 may be configured to provide a tensioning force on the drive wire 114 and the movable filament 122. In response to the tensioning force, the movable filament 122 may retract proximally, collapse the snare 116, and transition the distal ends of the branch members 118 to a more parallel configuration towards the longitudinal axis. In this example, the drive wire 114 may have suitable respective properties for transferring the pushing or tensioning forces e.g. flexibility, column strength, etc.

The filament 122 may be connected to the drive wire 114 in any suitable manner, such as via a crimp (not shown). The drive wire 114 may be connected to the plug 110 of the handle 106 to complete the electrical path from the plug 110 to the snare 116. All or a portion of the sheath 120, the branch members 118 that cover the movable filament 122, the crimp, and/or the drive wire 114 may be insulated using the insulator 136. The exposed portions of the filament 122, in some embodiments, may be the portions forming the snare 116, and those exposed portions may be used to make conductive contact with the surrounding tissue.

During collapsing of the snare 116, any tissue within or between the branch members 118 and the snare 116 may be grasped or ligated and electrosurgically cut and then retrieved. In some embodiments, the surface of the branch members 118 may be roughened, notched, slotted, flattened, or etched to provide better gripping surface for a more secured capture. In the device 101 of FIG. 1, the capture object can be released from the snare 116 through the distal end 104 or the space between the two branch members 118, if preferred.

In alternate embodiments, the snare 116 may be opened to make contact with the inner diameter of a vessel to electrically cut, or ablate the vessel from the inside out.

In the monopolar mode, the surgeon may use an active electrode in this case the exposed snare 116, to make contact with the tissue. The exposed portion of the snare 116 may be placed over the tissue to be cut and ligated. When the energy generator generates energy, electric current may flow from the active electrode, of the snare 116 through the body to the return electrode 111, and then back to the energy generator 126 producing an electrosurgical cut as the snare 116 is further collapsed.

In an another embodiment, during the bipolar mode of operation, the distal end 104 of the medical device 101 may include two separate filaments 122 acting as electrodes (not shown). Each of the filaments 122 may remain fixed at the distal opening 132 of another branch member 118. The ends 138, 140 of each of the filaments 122 disposed inside other branch member 118 may be connected to different couplers 142 of the energy generator 126. Further, the expandable snare 116 formed in bipolar mode may include portions including the insulator 136.

In the bipolar mode, voltage may be applied to the patient using a pair of similarly-sized electrodes, in which one electrode may include portions of half of the same snare, e.g. snare 116, while the other electrode may include portions of the other half of the same snare, i.e., snare 116. With half of the snare 116 connected to one pole of the energy generator 126 (for example, an alternating current generator 126) by means of another wire. When a piece of tissue is held by the snare 116, a high frequency electric current may flow from one to the other half of the snare 116, heating the intervening tissue producing an electrosurgical cut as the snare 116 is further collapsed.

Figure 4:
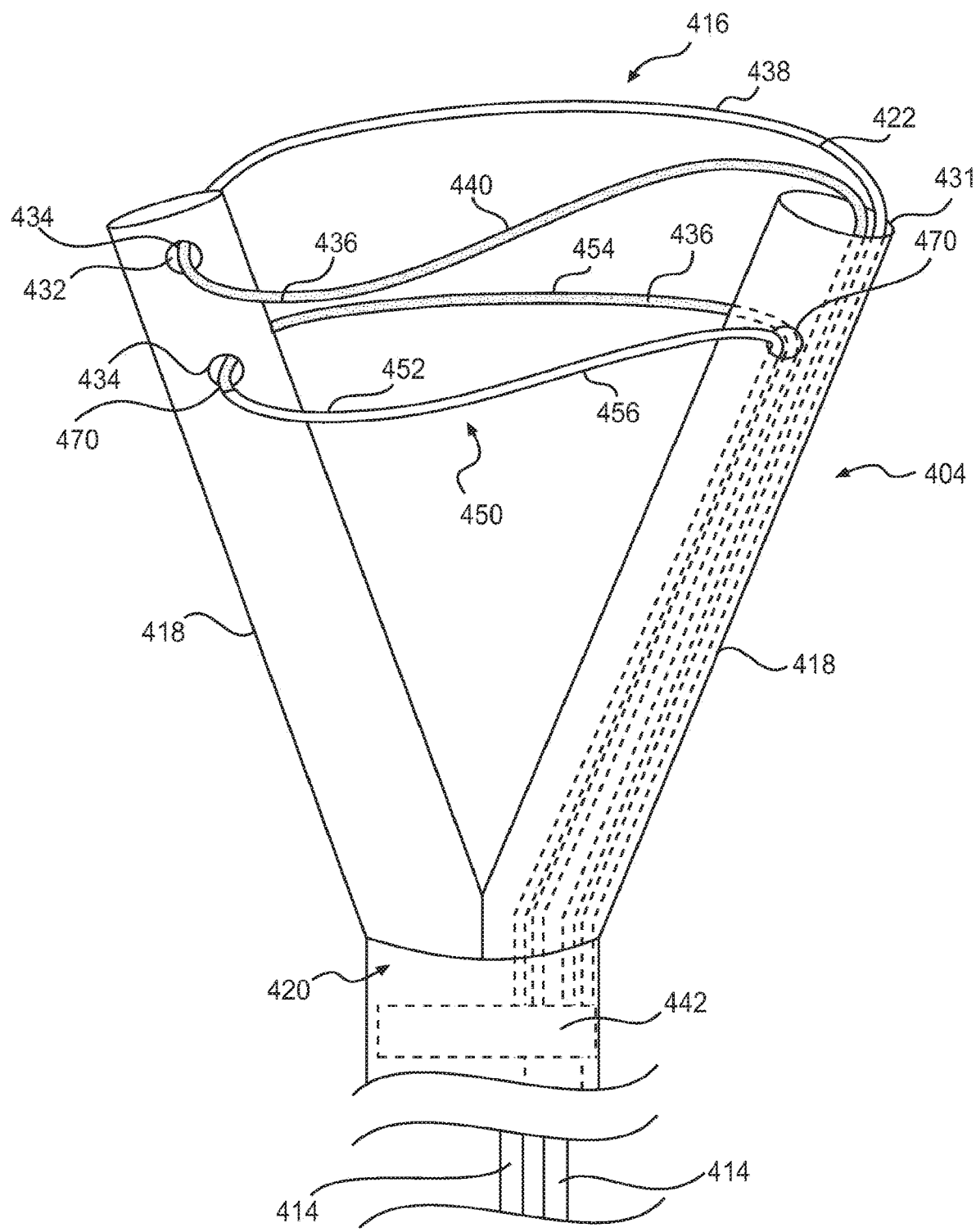
FIG. 4 illustrates a distal end of an exemplary medical device in an expanded configuration, in accordance with another embodiment of the present disclosure.

FIG. 4 illustrates a distal end 404 of an exemplary medical device (similar to the medical device 101) including a plurality of movable filaments such as a first filament 422 and a second filament 452 in an expanded configuration, in accordance with another embodiment of the present disclosure. The distal end 404 is similar in most respects to the distal end 104, except the distal end 404 may include two snares, a distal snare 416, and a proximal snare 450.

As shown, a plurality of movable branch members 418 may be disposed within or extend out of a sheath 420. One or more of the branch members 418 may include the one or more filaments such as the first filament 422 and the second filament 452. Each of the filaments 422, 452 may include two opposing ends. For example, the first filament 422 may include a first end 438 and a second end 440. Similarly, the second filament 452 may include a first end 454 and a second end 456. At least one of the branch members 418 may include a distal opening 431 and the other branch member 418 may include a distal aperture 432. Each of the branch members 418 may include a proximal opening 470 through which the filaments 422, 452 may pass through. In at least one embodiment, a portion of each of the movable filaments 422, 452 may be secured to the distal aperture 432 of the plurality of movable branch members 418. The two filaments 422, 452 may each form an expandable snare, such as, the distal snare 416 and the proximal snare 450.

Some portions of the filaments 422 and 452 that are proximal to the plurality of the expandable snares, such as the distal snare 416 and the proximal snare 450, may be selectively insulated using a suitable electrical insulator 436 to avoid any potential short circuit. In some embodiments a coated wire may include cuts such as skives or slots to expose the wire underneath the coating. In other embodiments a conductive metal may be plated onto plastic filament to creative a conductive pattern. The pattern may be straight or spiral or any preferred pattern. As shown in FIG. 4, in the expanded configuration, portions of snares 416 and 450 may be close to each other. For example, when expanded, portions of the second end 440 of the first filament 422 and the first end 454 of the second filament 452 may be close to each other. In order to avoid a short circuit, portions 440 and 454 of the filaments 422 and 452 may be insulated, while the first end 438 of the first filament 422 and the second end 456 of the second filament 452 may be active and act as electrodes. In this manner, the snares 416 and 450 may treat tissue and avoid a short circuit. The electrical insulation 436 (or insulator) may be deposited or coated on the filaments i.e. 422 and 452 in any suitable manner and may have any suitable pattern.

The actuation of the handle (for example, the handle 106) may displace the snares 416, 450 a similar amount to open or close both the snares 416, 450, simultaneously.

The two ends, first ends 438, 454 and second ends 440, 456, of the first filament 422 and the second filament 452, respectively, may extend from the fixed portion of the filaments 422, 452 secured to the branch member 418 and may enter a lumen of branch member 418 via either the distal opening 431 in the branch member 418, or the proximal opening 470. After entering into either opening 431 or 470 the two ends 438 and 440 of the first filament 422 and 454 and 456 of the second filament 452 may extend proximally through the lumen of the branch member 118 and connect to a drive wire 414 via a coupler 442 and the actuator 108 associated with a handle (for example, handle 106 of FIG. 1), so that the ends 438 and 440 and 454 and 456 move together with the actuator (such as, the actuator 108).

Further, each of the plurality of expandable snares 416, 450 (or filaments 422, 452) may be connected to different or the same connectors at the proximal end via the coupler 442. The coupler 442 may couple the filaments 422, 452 to the energy generator 126.

In some embodiments, a distal one of the plurality of snares 416, 450 may be configured to transfer energy and a proximal one of the plurality of snares 416, 450 may not transfer energy and may be configured to capture matter of the tissue. For example, the distal snare 416 may transfer energy and may be used for electro-cautery, while the proximal snare 450 may capture the matter of the tissue and may not transfer energy.

In some embodiments, one or more portions of the movable filament 422, 452 (or 122) may include one or more friction coatings and/or coatings having various properties such as: therapeutic, radiopacity, etc.

Further, the medical device as disclosed in FIG. 4, may operate in a monopolar mode and/or a bipolar mode. In monopolar mode, the first filament 422 may be fixed at the distal aperture 432 of one branch member 418 with two free ends insulated using the insulator 436 and disposed inside other branch member 418 via the distal opening 431. The two ends 438, 440 (acting as active electrode) of the filament 422 may be connected to one connector/terminal of the energy generator 126 (FIG. 1). Further, the return electrode 111 on the patient may be connected to other connector/terminal of the energy generator 126. The second filament 452 may be fixed at the proximal opening 470 of one branch member 418 with two free ends 454, 456 which may be insulated and disposed inside other branch members 418 via their respective proximal opening 470.

In the monopolar mode, the surgeon may use the exposed snare 416 or 450 to make contact with the tissue. The exposed portion of the snare 416 or 450 may be placed over the tissue to be cut and ligated. When the electric energy is turned on, the electric current may flow from the active electrode, through the body to the return electrode pad 111, and then back to the energy generator 126 producing an electrosurgical cut as the snare 416 or 450 is further collapsed.

In the bipolar mode, the free ends (i.e. 438, 440, 454, and 456) of each of the filaments 422, 452 may be connected to a different connector/terminal of the energy generator 126 or pairs of free ends may be connected to a different connector/terminal. Further, some portions of the filaments 422, 452 may be exposed i.e. may not have any insulation coating via a slit, a slot, a pattern, and so forth. Further, each exposed portion of the filaments 422, 452 may not be in contact with each other.

Figure 5:
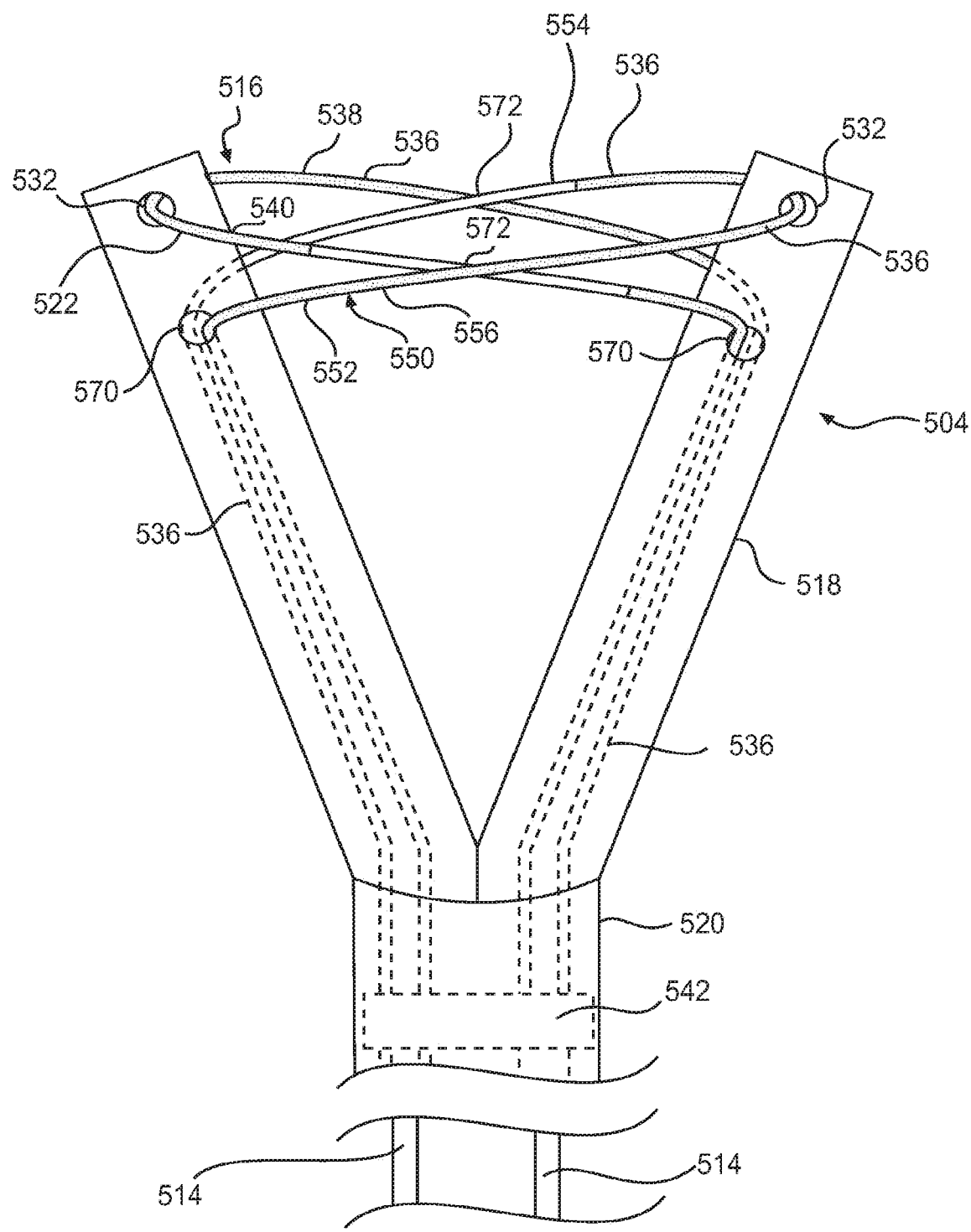
FIG. 5 illustrates a distal end of an exemplary medical device in an expanded configuration, in accordance with yet another embodiment of the present disclosure.

FIG. 5 illustrates a distal end 504 of another alternative exemplary medical device in an expanded configuration, in accordance with yet another embodiment of the present disclosure. The distal end 504 is similar in most respects to the distal end 104.

The distal end 504 may include movable filaments 522, 552 extending from a distal opening 532 of the branch member 518. Each of the one or more branch members 518 may include the distal opening 532 and a proximal opening 570. Further, each of the branch members 5108 may be disposed within a sheath 520 of suitable biocompatible material. The plurality of movable filaments 522, 552 may be coupled to one or more connectors 514 via a coupler 542 to transfer energy to the plurality of movable filaments 522, 552. The coupler 542 may couple the filaments 522, 552 to the energy generator 126. Further, when expanded, the movable filaments 522, 552 may form the plurality of snares, i.e., a distal snare 516 and a proximal snare 550. As shown, the movable filaments 522, 552 may form a loop and cross itself to form an intersection 572.

Each of the filaments 522, 552 may include a first end and a second end opposite to each other. For example, the first filament 522 may include a first end 538 and a second end 540. Similarly, the second filament 552 may include a first end 554 and a second end 556.

In some embodiments, one or more portions of the movable filaments 522, 552 (or the snares 516, 550) may include an insulator 536. In alternate embodiments, the one or more portions of the movable filaments 522, 552 may further include one or more friction coatings and/or coatings having various properties such as: therapeutic, radiopacity, and so forth.

The medical device of FIG. 5 may operate in a monopolar mode or/and a bipolar mode. In monopolar mode, the first filament 522 is fixed at the distal opening 532 of one branch member, such as first branch member 518 with two free ends, i.e. first end 538 and second end 540, which are insulated and disposed inside other branch members 518 via the proximal opening 570 of the other branch member 518. The free ends of the first filament 522 may be connected to one terminal/connector of the energy generator 126. A return electrode 111 on the patient may be connected to other terminal/connector of the energy generator 126. Further, the second filament 552 may be fixed at the proximal opening 570 of one branch member 518 with the two free ends 554, 556 insulated and disposed inside other branch member 518 via the distal opening 532 of the other branch member 518. The free ends 538, 540 of the first filament 522 may be connected to one terminal/connector of the energy generator 126. The snare 516 (or the proximal snare 550) may be completely exposed and there may not be any insulation coating over the snare 516 (or the proximal snare 550).

Further, in an embodiment, the distal snare 516 may be active and may be used for electro-cautery, while the proximal snare 550 may not be active and may only be used for holding the tissue/matter.

In the bipolar mode, the first filament 522 may be insulated using the insulator 536 and may remain fixed at the distal opening 532 of one of the branch members 518 with two free ends 538, 540 insulated and disposed inside other branch members via the proximal opening 570 of the other branch member 518. The free ends 538, 540 of the first filament 522 may be connected to a different terminal/connector of the energy generator 126. One or more portions of the first filament 522 may be exposed and may omit insulation. The second filament 552 may be insulated and may be fixed at the proximal opening 570 of one branch member 518 with two free ends 554, 556 insulated and disposed inside other branch member 518 via their respective distal opening 532. Further, each of the free ends 554, 556 of the second filament 552 may be connected to a different terminal/connector of the energy generator 126. One or more portions of the second filament 552 may be exposed and may omit the insulator 536 disposed on itself. Each exposed portion of the first filament 522 and the second filament 552 may not be in contact with each other.

Although the exemplary embodiments described above have been disclosed in connection with medical devices for providing electric energy treatment of human tissue through the working channel of a scope, a natural orifice, or by incision, but a person skilled in the art will understand that the principles set out above can be applied to any electro surgery device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A medical device, comprising:
   a handle having one or more connectors configured to be coupled to an energy generator;
   a sheath extending distally of the handle;
   a first moveable branch member and a second moveable branch member, a proximal end of each of the first moveable branch member and the second moveable branch member being coupled to a distal end of the sheath; and
   a plurality of filaments each having a midpoint and opposing end portions extending from the midpoint, the plurality of filaments contacting distal ends of each of the first moveable branch member and the second moveable branch member so as to form an expandable snare; and
   wherein the opposing end portions of the plurality of filaments each extend within a lumen of the first moveable branch member toward a proximal end thereof and connect to a single connector movably received within the sheath extending between the first and second moveable branch members and the handle and movable therewith relative to the first movable branch member and the sheath.

2. The medical device of claim 1, wherein at least a portion of at least one of the plurality of filaments is insulated.

3. The medical device of claim 1, wherein the opposing end portions of at least one of the plurality of filaments extend through a distal-most opening of the first moveable branch member.

4. The medical device of claim 1, wherein the opposing end portions of at least one of the plurality of filaments extend through a sidewall aperture of the first moveable branch member.

5. A medical device, comprising:
   a handle having one or more connectors configured to be coupled to an energy generator;
   a first moveable branch member and a second moveable branch member, a proximal end of each of the first moveable branch member and the second moveable branch member being coupled to a distal end of a sheath extending from the handle; and
   at least a first filament and a second filament, each of the first filament and the second filament having a midpoint and opposing end portions extending from the midpoint, wherein the opposing end portions of the first filament extend through a distal-most end of a lumen of the first moveable branch member and the midpoint is coupled to a sidewall aperture of the second moveable branch member, wherein the sidewall aperture is positioned proximally of a distal end of the second moveable branch member;
   wherein the opposing end portions of the first filament and the second filament connect to a single connector movably received within the sheath and movable therewith relative to the first movable branch member and the sheath.

6. The medical device of claim 5, wherein the opposing end portions of the second filament are each positioned within the lumen of the first moveable branch member at the proximal end thereof.

7. The medical device of claim 5, wherein the opposing end portions of the second filament are each positioned within a lumen of the second moveable branch member at a proximal end thereof.

8. The medical device of claim 5, wherein the distal end of the second moveable branch member and a distal end of the first moveable branch member are configured to flex radially outwardly from each other, and wherein the proximal end of the first moveable branch member and the proximal end of the second moveable branch member are axially fixed relative to the distal end of a sheath.

9. The medical device of claim 5, wherein at least a portion of at least one of the first filament or the second filament is insulated.

10. A medical device, comprising:
    a handle having one or more connectors configured to be coupled to an energy generator;
    a first moveable branch member and a second moveable branch member, a proximal end of each of the first moveable branch member and the second moveable branch member being coupled to a distal end of a sheath coupled to the handle so as to be axially fixed relative to the distal end of the sheath; and a plurality of filaments each having a midpoint and opposing end portions extending from the midpoint, wherein the plurality of filaments include at least a first filament and a second filament, wherein the midpoint of at least one of the plurality of filaments is adhesively secured to one of the first moveable branch member or the second moveable branch member;

wherein the opposing end portions of the plurality of filaments connect to a single connector movably received within the sheath and movable therewith relative to another of the first movable branch member or the second moveable branch member and the sheath.

11. The medical device of claim 10, wherein the opposing end portions of the first filament are each positioned within a lumen of the first moveable branch member at the proximal end thereof, and the opposing end portions of the second filament are each positioned within the lumen of the first moveable branch member at the proximal end thereof.

12. The medical device of claim 10, wherein the opposing end portions of the first filament are each positioned within a lumen of the first moveable branch member at the proximal end thereof, and the opposing end portions of the second filament are each positioned within a lumen of the second moveable branch member at the proximal end thereof.

13. The medical device of claim 10, wherein at least a portion of the at least one of the plurality of filaments is insulated.

14. The medical device of claim 10, wherein the opposing end portions of the at least one filament of the plurality of filaments extend through a distal-most opening of the another of the first movable branch member or the second moveable branch member.

* * * * *